United States Patent [19]
Bendzsak

[11] Patent Number: 5,245,279
[45] Date of Patent: Sep. 14, 1993

[54] APPARATUS AND METHOD INCLUDING FLUX INJECTOR POLE POSITION SENSORS FOR DETECTING PHYSICAL FLAWS IN FERROMAGNETIC OBJECTS

[75] Inventor: Gabor J. Bendzsak, Toronto, Canada

[73] Assignee: Niagara Mohawk Power Corporation, Syracuse, N.Y.

[21] Appl. No.: 900,304

[22] Filed: Jun. 18, 1992

[51] Int. Cl.5 .................. G01N 27/83; G01R 33/12
[52] U.S. Cl. .................. 324/225; 324/207.26; 324/227; 324/235; 324/262
[58] Field of Search .............. 324/220, 221, 225, 227, 324/232, 235, 242, 262, 207.11, 207.26

[56] References Cited

U.S. PATENT DOCUMENTS

| | | | |
|---|---|---|---|
| 2,226,725 | 12/1940 | Abbott et al. | 175/183 |
| 2,609,420 | 9/1952 | Watson et al. | 175/183 |
| 2,929,985 | 3/1960 | Havelka | 324/34 |
| 3,579,099 | 5/1971 | Kanbayashi | 324/235 |
| 3,710,236 | 1/1973 | Halsey et al. | 324/235 |
| 4,096,437 | 6/1978 | Kitzinger et al. | 324/227 |
| 4,215,310 | 7/1980 | Schwerer, III | 324/225 |
| 4,492,115 | 1/1985 | Kahil et al. | 73/151 |
| 4,507,610 | 3/1985 | Nakaoka | 324/228 |
| 4,510,447 | 4/1985 | Moyer | 324/225 |
| 4,528,506 | 7/1985 | Cavis et al. | 324/225 |
| 4,546,315 | 10/1983 | Lang | 324/262 |
| 4,555,665 | 11/1985 | Stanley et al. | 324/229 |
| 4,591,785 | 5/1986 | Hoehn, Jr. | 324/239 |
| 4,598,250 | 7/1986 | Lorenzi et al. | 324/220 |
| 4,659,991 | 4/1987 | Weischedel | 324/241 |
| 4,843,318 | 6/1989 | Greenblatt et al. | 324/225 |
| 5,041,786 | 8/1991 | Takaishi et al. | 324/240 |

Primary Examiner—Gerard R. Strecker
Attorney, Agent, or Firm—Heslin & Rothenberg

[57] ABSTRACT

A direct-current electromagnetic device for nondestructively detecting localized discontinuities in ferromagnetic objects is disclosed. The device comprises an adjustable dc excitor means, a magnetic flux injector means, an external magnetic field detector means, a plurality of position sensors, a signal processing means and a control means. It is particularly adapted for detecting flaws in soiled and distorted ferromagnetic objects such as water wall tubes in industrial boilers. An apparatus incorporating the device and a method of detecting discontinuities are also disclosed.

7 Claims, 5 Drawing Sheets

APPARATUS AND METHOD INCLUDING FLUX INJECTOR POLE POSITION SENSORS FOR DETECTING PHYSICAL FLAWS IN FERROMAGNETIC OBJECTS

BACKGROUND OF THE INVENTION

Field of the Invention

The present invention relates generally to direct-current electromagnetic testing devices and methods for inspecting magnetically permeable objects and, more particularly, to electromagnetic devices for detecting incipient flaws in soiled and distorted objects such as steel water wall tubes.

Information Disclosure

Boilers, such as those used for the commercial production of electricity, contain large areas for heat exchange between a heat source (fire) and a working fluid (water). The exchangers that line the sides of such boilers commonly take the form of "water walls", which are vertical steel tubes interconnected with a continuous steel web. During normal operation, the water walls are exposed to intense heat and mechanical wear. Therefore, periodic shutdowns of the boiler are scheduled to allow inspection and replacement of heat exchangers whose failure during subsequent normal operation would result in loss of generating capacity and expensive repairs. At present the inspection of water walls is either primitive (visual inspection and mechanical perturbation) or slow and expensive (ultra-sound). Since virtually all water wall failures occur on the fire side, a method and apparatus that could inexpensively and speedily probe the structural integrity of the face of the water wall would be highly desirable.

The fundamental problem that must be resolved by any proposed testing device based on electromagnetism relates to the inherent properties of steel. Under normal conditions, steel has high magnetic permeability which limits the extent of penetration of an external alternating current magnetic field. Thus, flaws that are embedded in the steel are difficult to locate by standard equipment based on inductance measurements as there is limited opportunity for the interaction between the field and the flaw. Furthermore, the size of a change in the external field is profoundly influenced by change in the permeability with the strength of the external field. Thus, under normal test conditions, it is difficult to determine whether a change detected as a result of moving a probe in the external field is due to a discontinuity in the steel or a minor change in the efficiency of injecting the field.

AC testing methods are generally used for non-magnetic materials, i.e. where the magnetic permeability is that of air. In this case, a change in the external field, caused by defects, is measured by a corresponding change in the inductance of a set of detector coils. Since the resistivity is the only material property of concern, it is not difficult to adjust the frequency of the exciting current to the value required for the detection of defects. These devices work at low values of exciting fields and require very little power.

The picture changes completely for testing of ferromagnetic materials. Consider the equation relating depth of penetration ($\delta$) to the relative permeability of steel ($\mu_r$), the permeability of air ($\mu_o$), the frequency (f) and the conductivity ($\sigma$):

$$\delta = \sqrt{\frac{1}{\mu_o \mu_r \pi f \sigma}} \quad (1)$$

In steels, $\mu_r \gg 1$ and $\delta$ is small at any practical frequency. In this case, the exciting AC fields are confined essentially to narrow surface layers facing the excitor side. Since the penetration varies as a function of $$\frac{1}{\sqrt{f}} \quad (2)$$

significant penetration can occur at very low frequencies, but at low frequencies the measurements are influenced by factors other than those arising from flaws. Thus, changes in the impedances of external coils are small, difficult to relate to root causes, and reflect primarily surface phenomena. Although the drawbacks in testing ferromagnetic objects render AC excitors generally unattractive for testing for subsurface discontinuities, some AC devices are known.

U.S. Pat. No. 2,226,275 (Abbott et al.) discloses an apparatus for measuring the thickness of magnetic materials. The apparatus comprises a continuous pole piece or yoke in the form of a cylinder having a closed end portion. Positioned in concentric relation with the yoke and in engagement with the yoke is a laminated core structure or pole piece. The arrangement employing a central core and an outer surrounding pole piece confines the magnetic flux, which is provided by a direct current winding. An AC driven magnetic circuit is used to measure the potential variation in a secondary winding due to variations in thickness of the test object. A second U-shaped embodiment of the gauge head is also disclosed for use with tubes having an extremely high ratio of wall thickness to diameter. The AC coils basically form a transformer whose output voltage depends on the thickness of the test piece. In the Abbott device the coupling between the coils becomes increasingly poor as the thickness of the plate is decreased. The device is relatively insensitive to small changes in thickness and profoundly sensitive to variations of flux density within a thick wall.

U.S. Pat. No. 2,609,420 (Watson et al.) discloses a device similar in basic design and principle to that of Abbott et al. In the Watson device, magnetic flux is measured across an angular non-magnetic gap in the interior of the device where the induced magnetic flux returns to the coil.

U.S. Pat. No. 2,929,985 (Havelka) discloses a pure AC method for measuring wall thickness in ferromagnetic objects. It relies on detecting eddy currents induced by a fluctuating magnetic field.

U.S. Pat. No. 4,215,310 (Schwerer) discloses a method and apparatus for electromagnetic testing of magnetically conductive materials. Properties of the test pieces are determined by applying a controlled alternating drive current to an excitation coil so as to produce a predetermined AC voltage in the pickup coil and measuring the drive current applied to the excitation coil when the time integral of the voltage induced in the AC pickup coil corresponds to zero magnetic flux in the gaps between the end faces or poles of the probe and the surface of the test piece.

U.S Pat. No. 4,492,115 (Kahil et al.) discloses a method and apparatus for determining the extent of defects in ferromagnetic tubular elements. The device measures tubing average wall thickness, local defects such as corrosion pitting and axial, defects. The device includes two separate field-generated coils, two separate detecting coils and a plurality of discreet detecting elements. The AC magnetic detecting coils, the flux leakage detecting probes and the velocity detector are radially spaced from the tubing in which defects are to be measured. In order to obtain full coverage of the tubular section and to obtain a measurable response, the preferred embodiment of the invention comprises an apparatus for rotating the fluctuating AC magnetizing field around the tubular work piece as the tubing section moves axially relative to both the AC magnetizing field and the uniform DC saturating magnetizing field.

U.S. Pat. No. 4,507,610 (Nakaoka) discloses a method of electromagnetically detecting flaws in a metallic object. An electromagnetic coupling coil is supplied with a high frequency current to produce a high frequency magnetic field which closely links with a sensor ring. Since the ring forms a circuit closed or almost short-circuited by the sensing head, a large amount of current is induced in the sensor ring and flows to the sensing head. As a result a magnetic field is produced. The magnetic field excites the object so that a current is induced locally in the area of the object being tested immediately below the sensing head. When a defect or flaw occurs immediately below the sensing head, the electromagnetic coupling between the sensing head and the object changes with a resulting minute change in the amount and phase of the current flowing through the sensor ring. Because the Nakaoka device uses a high frequency magnetic field only surface defects will be detected.

U.S. Pat. No. 4,510,447 (Moyer) discloses an apparatus for detecting flaws in the wall of a ferromagnetic pipe. The apparatus comprises an electromagnet having poles in slidable contact with the surface of the wall to form a closed magnetic circuit. The electromagnet is energized by a source of alternating current to produce a fluctuating magnetic field axially through the wall of the pipe between the poles of the electromagnet. Means adjacent to the surface of the wall of the pipe between the poles of electromagnet sense leakage of the magnetic field from the pipe and generate a signal corresponding to a sensed portion of the leakage.

U.S. Pat. No. 5,041,786 (Takaishi et al.) discloses a method of inspecting a ferromagnetic work piece by examining the eddy currents induced in the work piece. The object to be inspected is passed through an excitation coil; the excitation coil is driven by an AC power source and rotated so as to sweep the peripheral surface area of the work piece at a predetermined distance. A detection coil detects changes in the magnetic field produced by an eddy current induced by the AC excitation.

Because of the shortcomings of AC devices, test apparatus that utilize DC or permanent magnets are also known.

U.S. Pat. No. 4,546,316 (Lang) discloses a testing device for testing wire rope in an aerial tram system. The device comprises an upper housing which contains strong permanent magnets. These act as north and south poles in establishing a magnetic field through the wire rope at the rope section located between the pole pieces. Between the poles and completely surrounding the wire rope is a detector coil of undisclosed nature that picks up leakage from the main magnetic field as it passes through the coil.

U.S. Pat. No. 4,555,665 (Stanley et al.) discloses a device for indicating wall thickness in a length of ferromagnetic element. An axially split sleeve or spool is clamped in surrounding relationship to an installed pipe. A saturation level of magnetic flux is induced in the pipe by passing DC current through a multi-turn coil. One or more pickup coils are then mounted in surrounding relationship to the spool and a separate multi-turn current path is provided through each of the pickup coils. The resulting integrated signal provides a reading of the average thickness of the pipe around the angular section encompassed by the pickup coil at any time. The device must be clamped around the object to be tested and does not provide information on radial flaws.

U.S Pat. No. 4,096,437 (Kitzinger and Wint) discloses a testing device comprising a permanent magnet assembly having poles adapted to be spaced apart in the longitudinal direction of an elongated object for inducing a longitudinal magnetic flux in a section of the object between the poles of the magnet. The work piece is magnetically saturated and Hall-effect devices are spaced around at least one pole piece in the path of the magnetic flux for sensing the radial flux entering the elongated object. An additional Hall sensor may be provided located between the pole pieces for detecting external and internal defects in the object. The device as disclosed surrounds the object to be tested. In addition, the magnetic flux detected by the Hall-effect devices will be a function not just of the magnetic permeability and cross-sectional area of the test object but also the efficiency of the injection of the magnetic flux by the permanent magnet assembly which is in turn a function of the gap between the pole piece and the ferromagnetic test object.

U.S. Pat. No. 4,591,785 (Hoehn) discloses a method of measuring hardness in steel casings. A detector employs a steel core surrounded by a magnetizing coil and the detecting coil. A current (not specified) is passed through the magnetizing coil to create a magnetizing force. The detector is passed along a length of steel that is to be tested to create a flux flow through the steel core and the steel to be tested. The current induced in the detecting coil in response to the flow through the steel core is detected as a measure of the hardness of that portion of the test object subjected to the magnetizing force.

U.S. Pat. No. 4,598,250 (Lorenzi and Wagerer) discloses a corrosion probe which is hauled through the inside of a ferromagnetic pipe. The device consists of a pair of permanent magnets disposed side-by-side in parallel relation with the south pole of one magnet adjacent the north pole of the other magnet. A coil wound on a bobbin is disposed around the lower ends of the magnets within a housing. The sensor operates as a leakage flux device. On a smooth surface the magnetic flux through the coil is constant and no voltage is induced in the coil. When the sensor moves over a corrosion pit, the magnetic field through the coil will decrease as the first magnet moves over the pit and then increase as the second magnet moves over the pit to produce a field variation with time.

U.S. Pat. No. 4,659,991 (Weischedel) discloses a device for inspecting elongated objects such as wire cables. The device comprises a permanent magnet for inducing a saturated magnetic field axially through the work piece in the longitudinal direction. A sensing coil is located at a position midway between the poles of the magnet and lies in the plane perpendicular to the longitudinal axis of the work piece. The coil circumscribes substantially the entire circumference of the work piece in close proximity to the exterior surface and detects changes in leakage flux as the work piece and the device move relative to one another in the longitudinal direction.

The characteristics that have prevented the commercial use of prior art devices for testing water walls and similar ferromagnetic structures having only one accessible face fall into three categories: (1) they use AC excitors that detect only surface phenomena; (2) they must encircle the test piece; or (3) the signal that is obtained can only be correlated to structural phenomena when the magnetic field arising from the injected magnetic flux is otherwise constant. This third characteristic creates problems in boilers because the water walls accumulate surface deposits of soot and scale that alter the efficiency of injection of the magnetic field from the excitor. The problem can be circumvented so that known devices can be used, but the required scrupulous cleaning of surfaces inside boilers is expensive and time-consuming. In addition, the intense heat and stress in the interior of a boiler in normal use lead to distortions of the water wall from its original design shape (warping and lateral displacement) that make the correlation of spacial coordinates in a magnetic field problematic.

Thus there is a need for a rapid, inexpensive nondestructive system that can detect subsurface flaws and discontinuities in sooty or scale-flecked steel water walls in situ in a boiler.

SUMMARY OF THE INVENTION

It is an object of the present invention to provide an apparatus that can detect subsurface flaws in ferromagnetic objects.

It is a further object to provide an apparatus that can reliably detect flaws in ferromagnetic objects only one of whose surfaces is accessible.

It is a further object to provide an apparatus that is compliant so that distortions in geometry of the ferromagnetic object can be accommodated.

It is a further object to provide an apparatus that can compensate for surface deposits on the ferromagnetic object so that variations in an induced external magnetic field that arise from internal discontinuities are not confused with variations that arise from the efficiency of injection of the induced field into the object.

These and other objects are realized in the instant invention.

In one aspect the invention relates to an electromagnetic device for nondestructively detecting localized discontinuities in ferromagnetic objects comprising:

(1) an adjustable direct current exciter means for generating a high intensity magnetic field;

(2) an injector means for magnetically saturating a segment of a wall of a ferromagnetic object. The injector means has two opposite magnetic poles spaced from one another for inducing in a segment of the object between the poles, a magnetic flux above the saturation level. The injection means also defines a ferromagnetic flux return path between the poles externally of the object for completing the flux circuit;

(3) a detector means for measuring the magnetic flux on the exterior of said ferromagnetic object and sending an output signal indicating the magnitude of said flux at a point to a signal processing means;

(4) a plurality of position sensors mounted in close proximity to said injector means. The position sensors send an output signal to a signal processing means indicating the relative location of the injector magnetic poles with respect to said object;

(5) a signal processing means for receiving and storing the output signals from the detector means and from the position sensors. The signal processing means is capable of calculating changes in the displacement of the injector means and is capable of generating an output signal to adjust the exciter means to compensate the amount of field being generated in order to provide a substantially constant flux in the object. The processing means is further capable of comparing stored detector signals with incoming detector signals and of displaying an output; and (6) a control means for adjusting the exciter means according to output signals generated by the signal processing means. The detector means is capable of measuring tangential and normal components of flux. The presently preferred embodiment utilizes the tangential component. It is preferably a plurality of Hall-effect devices. The position sensors are preferably a pair of L-shaped, polarized force transducers each having two ends, one of which is attached to a permanent magnet, the other of which is rigidly fixed to a pole of the injector means.

In a further aspect the invention relates to an apparatus for examining a water wall in a boiler comprising a device as described above and a framework. The framework provides a controlled displacement of the device in three dimensions.

In a further aspect the invention relates to a method for testing a segment of a ferromagnetic object comprising:

(1) saturating the segment with a constant but adjustable magnetic flux. The flux is provided by a direct-current coil and a bipolar injector in contact at two points on a surface of the ferromagnetic object;

(2) positioning a plurality of Hall-effect devices adjacent the surface of said ferromagnetic object within the path of the magnetic flux so as to detect the strength of an exterior magnetic field generated by the saturating magnetic flux;

(3) determining the position of each pole of the bipolar injector in respect to the surface of said object;

(4) adjusting the direct current supplied to the coil to compensate for a change in proximity of the device relative to the ferromagnetic surface so as to maintain a substantially constant magnetic flux in the segment of interest; and (5) reading an output from the plurality of Hall-effect devices to determine the contour of the exterior magnetic field.

DESCRIPTION OF PREFERRED EMBODIMENTS

Figure 1:
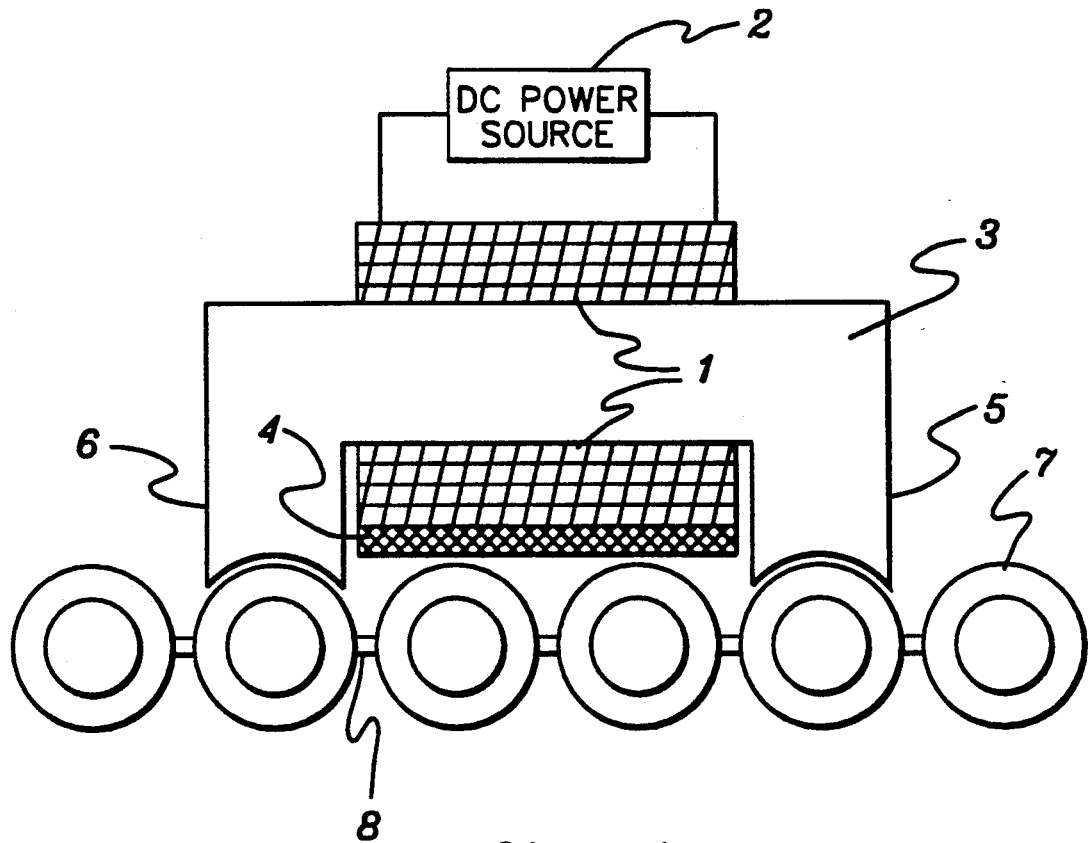
FIG. 1 shows a horizontal cross-section of a device of the invention and an adjacent water wall.

The basic electromagnetic features of a testing device for the ferromagnetic walls of utility boilers are shown in FIG. 1. A high intensity magnetic field is generated by the windings of a coil 1 connected to an adjustable current power source 2. The magnetic field generated by this winding is injected into the tubes 7 of the water wall through a path provided by a yoke 3 made of iron exhibiting high relative permeability. The ends 5 and 6 or poles, of the yoke in the figure are contoured to fit the crown of a tube 7 in a water wall, but may be provided with other contours for testing other ferromagnetic objects. Since the magnetic reluctance of the yoke is much lower than that of the tube, when the yoke is in direct contact with the tube most of the flux generated by the coil is forced to enter the tube. The strength of the flux is adjusted such that the steel of the tube wall and the connecting web 8 is in a magnetically saturated state. A field then leaks from the tubes into the outside air. A row of Hall effect devices 4, placed in the immediate vicinity of the tubes, measures the intensity and distribution of this field. The normal variation of the leakage field represents a characteristic signature that can be used for the continuous evaluation of tube wall mechanical integrity.

Figure 7:
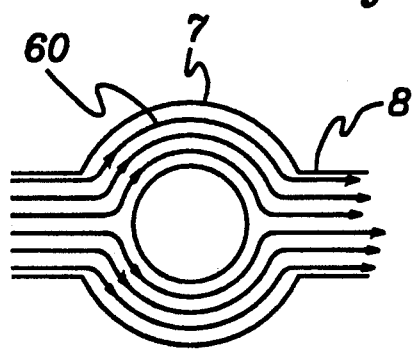
FIG. 7 and FIG. 8 are cross-sections of a tube showing the magnetic flux.
Figure 8:
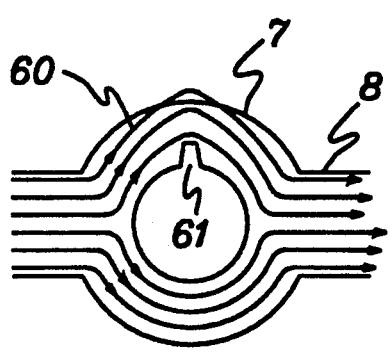

FIG. 7 shows a cross-section of steel tube 7 and associated web 8 in a magnetically saturated state with the magnetic flux shown as lines 60 passing from left to right. In the absence of a flaw, the flux remains predominantly within the steel web and tube. In FIG. 8 a flaw 61 is introduced on the interior of the crown of the tube, a common locus for flaws. The presence of a flaw increases the magnetic reluctance in a discrete region of the tube wall. Flux density increases in the region near the flaw resulting in a deeper saturation of the steel. As a result, the flux splits, part shifting to the far side of the tube, and the other part increasing the leakage component under the Hall effect sensing devices. Since the steel tube is initially saturated, the shunting path through the air becomes increasingly significant, and the sensors will detect an increased leakage flux in the region of the defect. Both gradual wall wear and crack formation will cause an increase in the air gap flux density.

The principles outlined above are known to be applicable to the problem of detecting discontinuities in ferromagnetic objects. The difficulty with their application heretofore in practical situations has arisen from two sources: (1) the assumption of a constant flux in the test object, and (2) the assumption of an exterior field of uniform contour in the absence of a discontinuity in the test object. Detectors of the art for ferromagnetic objects operate on the assumption—which is true for most ferromagnetic objects—that irregularities in the magnetic fields will reflect internal discontinuities because the test object is unchanging in contour, and clean. The objects to be tested by the device of the invention are neither.

The provision of a constant flux in the test object is relatively straightforward when the test object is clean and smooth, so that the injector poles 5 and 6 can make good contact with the object. However, when a pole is forced away from the ferromagnetic object, as for example by a patch of soot or scale, any intervening nonferromagnetic gap will cause the magnetic flux in the object to decrease. The Hall-effect sensors then register a decrease in external field which has nothing to do with a structural defect. The device of the invention surmounts this problem by determining the distance of the pole from the substrate, calculating the loss of flux that would result, and increasing the drive current to the excitor to compensate. The external field thus remains substantially constant even when the device is resting on a patch of soot or scale. A 3 mm lift-off is the practical upper limit of modulation of the injected flux in the present embodiment of the invention.

The provision of a geometrically regular external field is similarly straightforward when the test object is geometrically regular. Unfortunately, water walls become geometrically distorted (without losing structural integrity) during use, and the test device must distinguish between changes in the contour of the external magnetic field that arise from structural flaws and changes that arise from geometric distortion. The device of the invention accomplishes this by determining where each reading is taken in relation to a common reference, in this case the center line of a tube 7.

Figure 2:
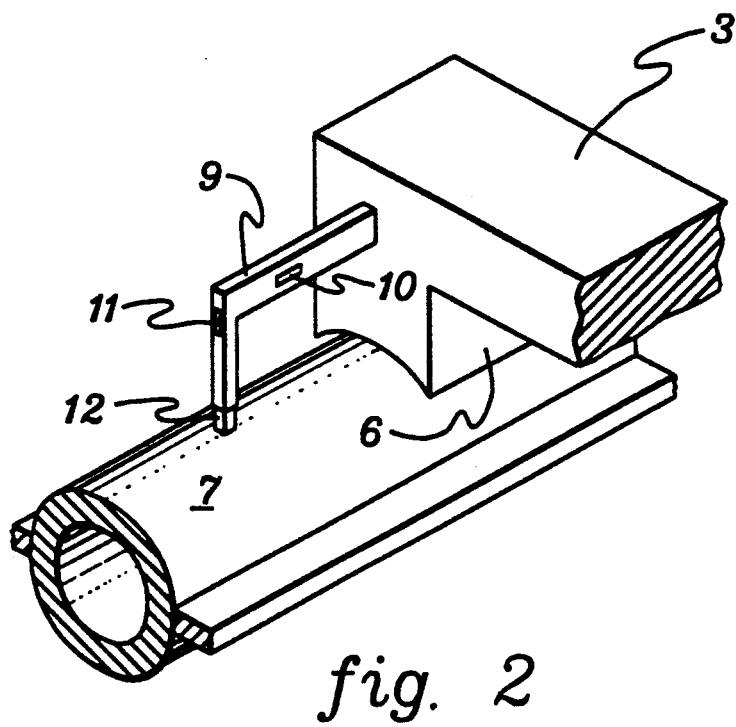
FIG. 2 is an oblique view of a single tube of a water wall and a single pole of an injector showing the position sensors in more detail.

The two compensations that enable the device of the invention to provide meaningful output from soiled and distorted water walls are accomplished by providing a plurality of position sensors 9 rigidly attached to the injection poles 5 and 6. Sufficient positional information is obtained from two such sensors, but more can be added if finer resolution is desired. The use of two force transducers of the general design shown in FIG. 2 provides information on positive and negative excursions along either of two axes: x (lateral movement) and z (movement normal to the water wall). FIG. 2 shows a schematic for mounting a transducer 9 over the tube crown 7. The transducer is attached to one leg 6 of the magnetic yoke 3 of FIG. 1. The forces exerted on a permanent magnet 12 by the wall are resolved into two components by strain gauges 10 and 11. Gauge 11 measures the normal force; gauge 10 measures the transverse force. Deviations in the outputs of strain gauge 11 indicate changes of the transverse position of magnetic exciter with respect to the crown of the tube. In its normal position, centered over the crown of a tube and resting on it, the force exerted on the permanent magnet 12 is zero. As a transverse movement occurs and the magnet follows the crown, the force exerted on transducer 9 increases. The strain gauge signal changes polarity as the strain is deflected from side of the tube to the other indicating the direction of displacement of the magnet.

Consequently, the outputs of the force transducers will give unambiguous signals to correct the readings of the Hall effect probes and to steer the detector along the tube crown. The magnitude of force in the normal direction, as measured by strain gauge 10, is directly related to the distance away from the tube crown.

Changes occurring in the magnitude of the output signal of strain gauge 10 indicate lift-off of the yoke with respect to the magnetic surface of the tube. The signal can be used to deduce the thickness of dirt and/or slag over the tube, and the loss in flux within the wall associated with a lift-off can be automatically compensated by an increase in coil current. There are limits to this compensation that are imposed by the proximity of the Hall-effect detector means. As more magnetic flux from the yoke is driven against higher impedance at the junction, more leakage occurs at the junction and eventually the magnitude of this leakage will be such that flux from this source will impinge on the detectors.

The position sensors in the preferred embodiment are L-shaped force transducers incorporating permanent magnets, however the invention is not restricted to such sensors. Any device that can resolve the x and z components of displacement would work. For example sensors that utilized inductance coils to sense a change in inductance that resulted from a change in coupling between the sensor and the tube are possible, but precise readings are more difficult to obtain because partially magnetic residue on top of the tube confuses the sensor. Readings from optical and acoustic sensors need to be made from the tube surface and not the soot or slag surface, which makes them less straightforward.

Figure 3:
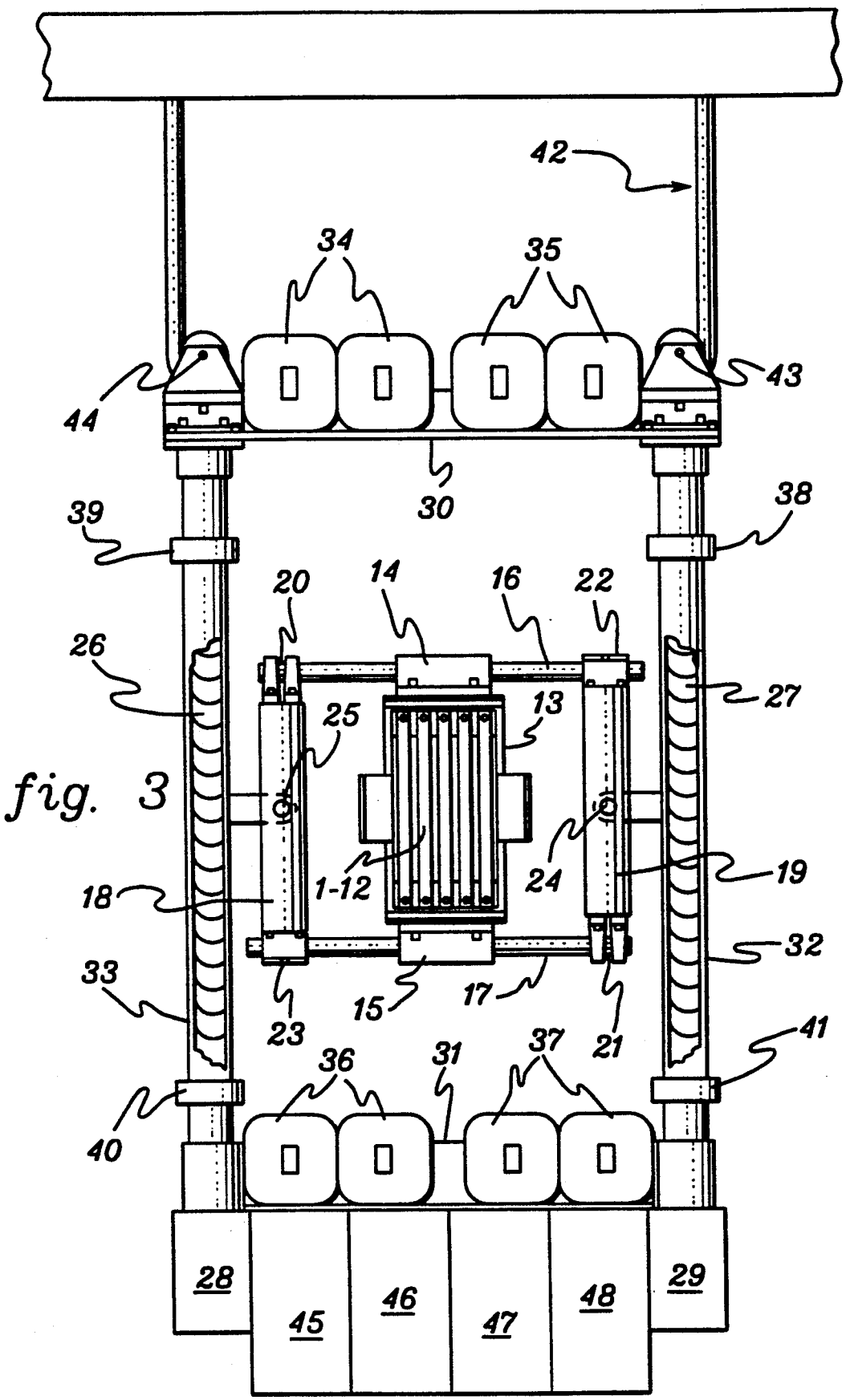
FIG. 3 is a front view of an apparatus for examining a water wall. The apparatus comprises a device for inducing and measuring a magnetic field and a framework to provide controlled displacement of the device with respect to the water wall.

An assembly consisting of the coil, the yoke, the Hall probes of FIG. 1, and a set of force transducers of FIG. 2, will be referred to as the testing head. The incorporation of this testing head into a machine for testing water walls is shown in FIG. 3 (front view) and FIG. 4 (side view). The whole machine is suspended from a hoist placed in the upper reaches of the boiler. The operation of this hoist is coordinated with movements required for the placement of the complete system along the boiler water wall.

Referring to FIG. 3, the testing head 1-12 is placed within a frame 13 surrounding it. Frame 13 is attached to two sleeve bearings 14 and 15 which are free to slide over two horizontal bars 16 and 17. One end of each of these bars is firmly fixed to vertical arms 18 and 19 at points 20 and 21. The other ends are free to move in sleeve bearings 22 and 23. The vertical arms 18 and 19 in turn are attached to two pillow blocks 24 and 25. The pillow blocks are moved by spirally threaded rotating shafts 26 and 27 that are driven by two precision stepping motors 28 and 29. The distances between shafts 26 and 27 are maintained by two horizontal cross bars 30 and 31 that are rigidly connected to the housings 32 and 33 of shafts 26 and 27. Consequently, a solid outer frame is provided by cross bars 30 and 31 and the housings 32 and 33 of vertical rotating shafts 26 and 27. The inner framework, consisting of vertical arms 18 and 19 and horizontal bars 16 and 17 can rotate to a certain extent in the x-y plane using pivots 24 and 25. Thus differential activation of stepping motors 28 and 29 will rotate the testing head in relation to the water wall tubes. This motion will allow the testing head to follow local tube distortions from the vertical and to correct for skewed motion of the whole unit. Required horizontal movements are implemented by moving the testing head 1-12 along bars 16 and 17.

While measurements are Conducted, the outer frame is held securely against the water wall tubes by means of four magnetic feet 34-37. When limit switches 38 and 39 sense the presence of pillow blocks 24 and 25, electronic signals activate the hoist, and move the entire machine by adjusting the length of cable 42. The testing machine is attached to the cable by two pulleys 43 and 44. The electronic systems required for motor control, position sensing, and signal conditioning of the Hall probe outputs are housed in boxes 45-48. Computer and power cables are also attached to these boxes.

Figure 4:
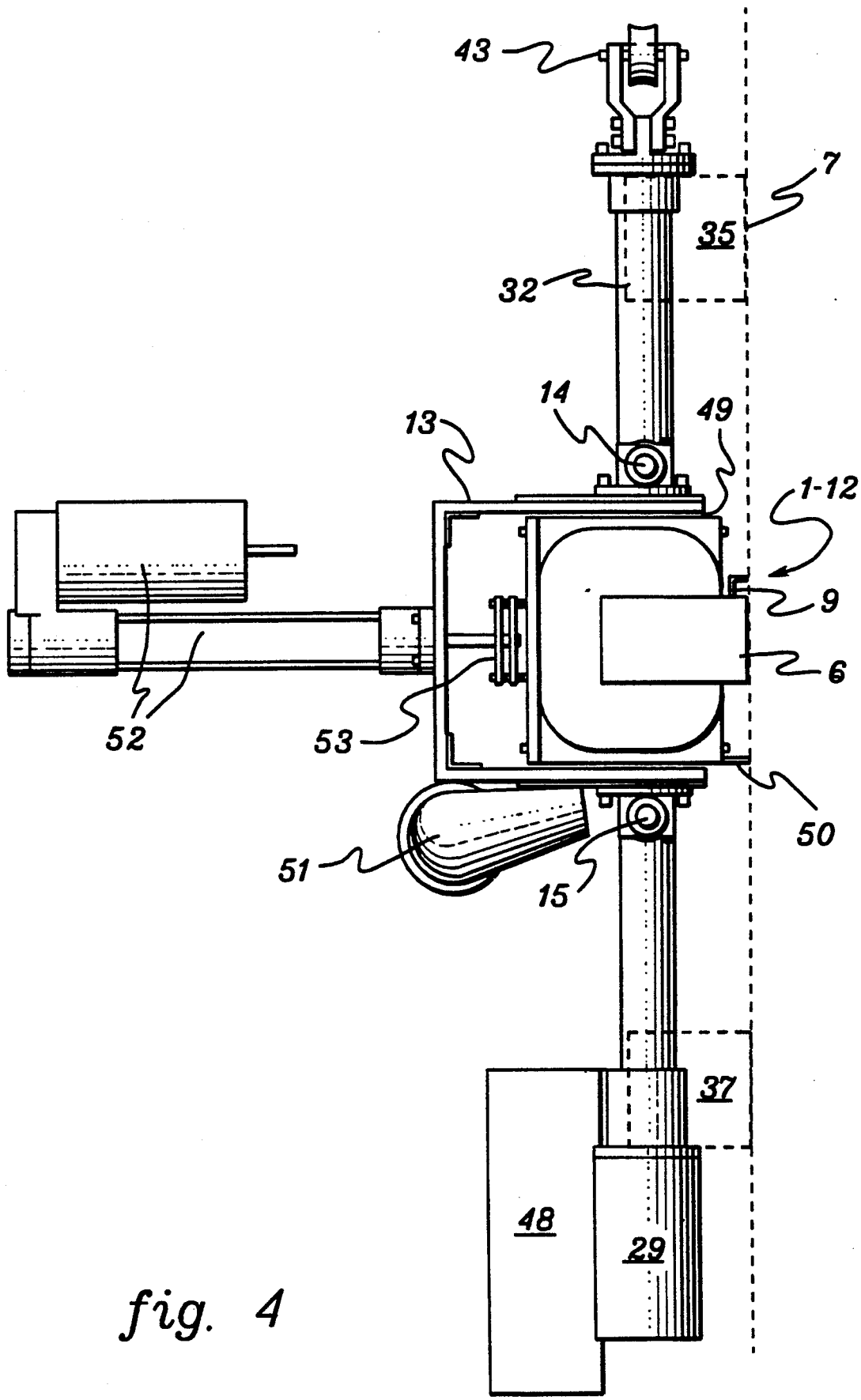
FIG. 4 is a side view of the apparatus of FIG. 3.

A side view of the device is shown in FIG. 4. The testing head 1-12 is positioned in a frame 13 where it is free to pivot about the vertical axis by means of two sliding discs 49 and 50. The magnetic feet to attach the frame to the wall are indicated by the dotted boxes 35 and 37. The location of the tube crown is given by the dotted line 7. The sleeve bearings used to allow horizontal motion are indicated by 14 and 15.

A stepping motor 51 controls the horizontal motion of the testing head. Its shaft is rigidly attached to frame 13. The motion of the head towards and away from the tube wall is achieved by a stepping actuator 52 mounted on frame 13. The shaft of actuator 52 is attached to a spring loaded housing 53 connected to the testing head. By controlling actuator 52, the testing head can be moved close to the tube. On energization of the power coil 1 within the head, pole 6 comes into intimate contact with the boiler tube crown 7. On de-energization, the springs in assembly 53 separate the head from the tubes and the machine is free to make a move dictated by the control system.

Figure 5:
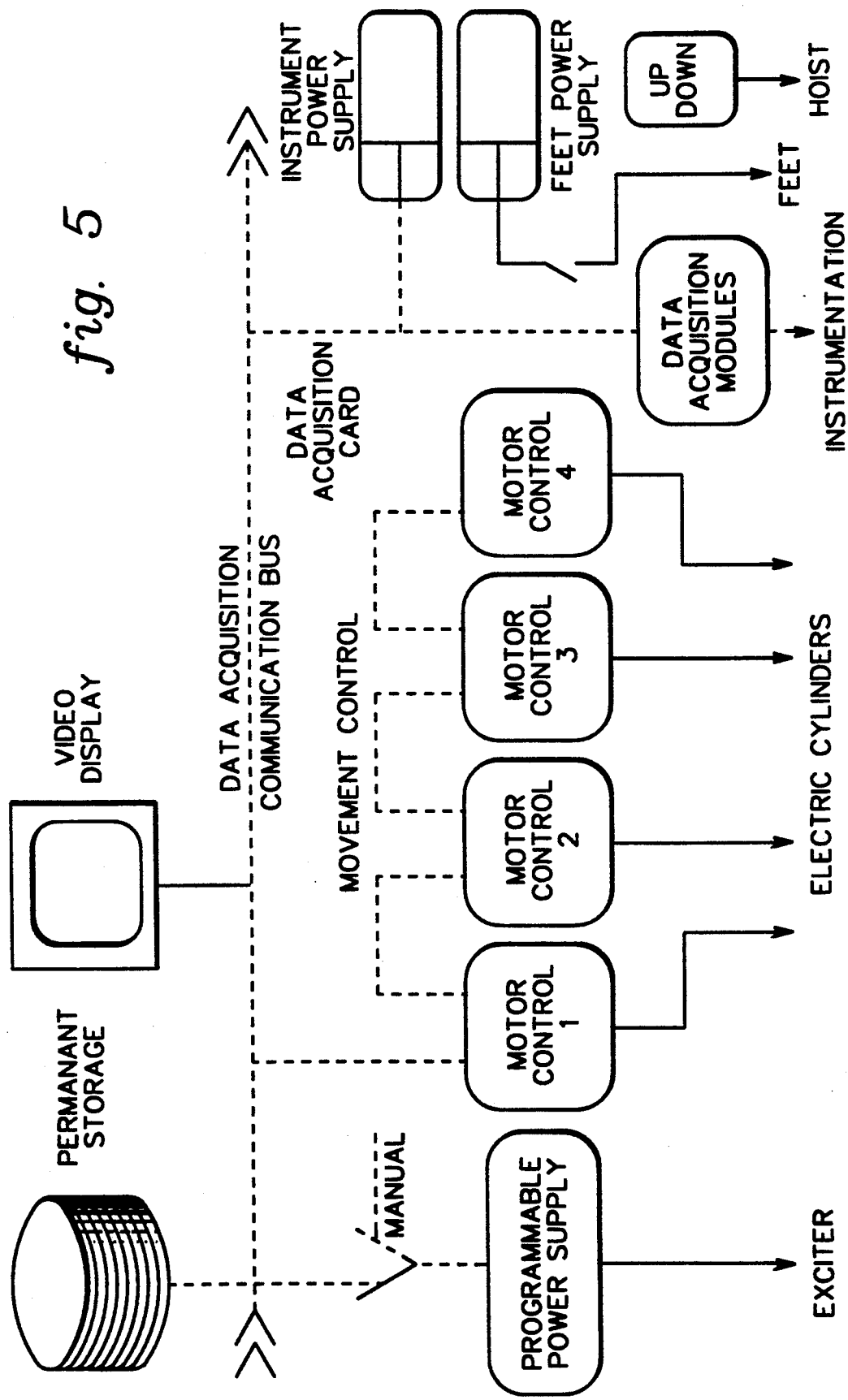
FIG. 5 is a schematic diagram of the control system for the apparatus of FIG. 3.

An electronic control system is required for the collection, interpretation and storage of data obtained from the Hall effect devices and the force transducers. In addition, the motion of the testing machine has to be controlled precisely to eliminate spurious readings of the sensors. Machine control and data acquisition is outlined in the block diagram of FIG. 5. The creation of appropriate algorithms for the handling of input signals and the conversion of those signals to output data and signals are within the skill of the ordinary artisan.

The operation of the machine can be either automatic, semi automatic, or manual, but the device will be operated most of the time in automatic mode. At the start of each cycle the magnetic feet 34-37 are energized and the testing machine is held firmly against the water wall tubes. The weight of the device is supported by the cable 42 connecting the machine to the hoist. The electrically de-energized testing head 1-12 is in the immediate vicinity of the tube crown 7. At this time the force transducers 9 are interrogated and a decision is made whether or not a minor machine motion is required to obtain a better tube to head alignment. After completion of the required movements, the magnitude of the coil current is determined and the output of the programmable DC power supply 2 is energized. As the testing head is attracted to the ferromagnetic wall, the outputs of all power supplies for stepping motor control are de-energized. This ensures the elimination of high frequency electromagnetic interference from the outputs of the Hall sensors.

The outputs of all Hall effect devices 4 are scanned and relayed to the computer. A comparison of the readings is made with respect to the previous values, and the result is presented in a graphical mode for easy interpretation. The readings are labelled and stored in a data base. The coil 1 of the testing head is de-energized, and the control motor power supply outputs are enabled. The sensing head is moved away from the tubes to a predetermined position, and the vertical control screw stepping motors 28 and 29 are advanced to the position required for the next measurement. On completion of the vertical motion, the test cycle repeats itself until the upper limit switches 38 and 39 indicate the end of travel.

On activation of the upper limit switches 38 and 39, the coil 1 of the testing head is energized, and the power to the stabilizing feet 34-37 is disconnected. The stepping motors 28 and 29 of the vertical screws are engaged for a rapid reverse motion to drive the frame 16–19 upward. The cable slack is taken up by the hoist, always under slight tension. The drives are activated until he lower limit switches 26 and 27 indicate the end of travel. At this time a command is given to stop the hoist and energize the coils of the magnetic feed 34–37. Since the testing head is firmly attached to the wall during the entire procedure, its position is always remembered. On the re-attachment of the magnetic feet, a new cycle begins.

Figure 6:
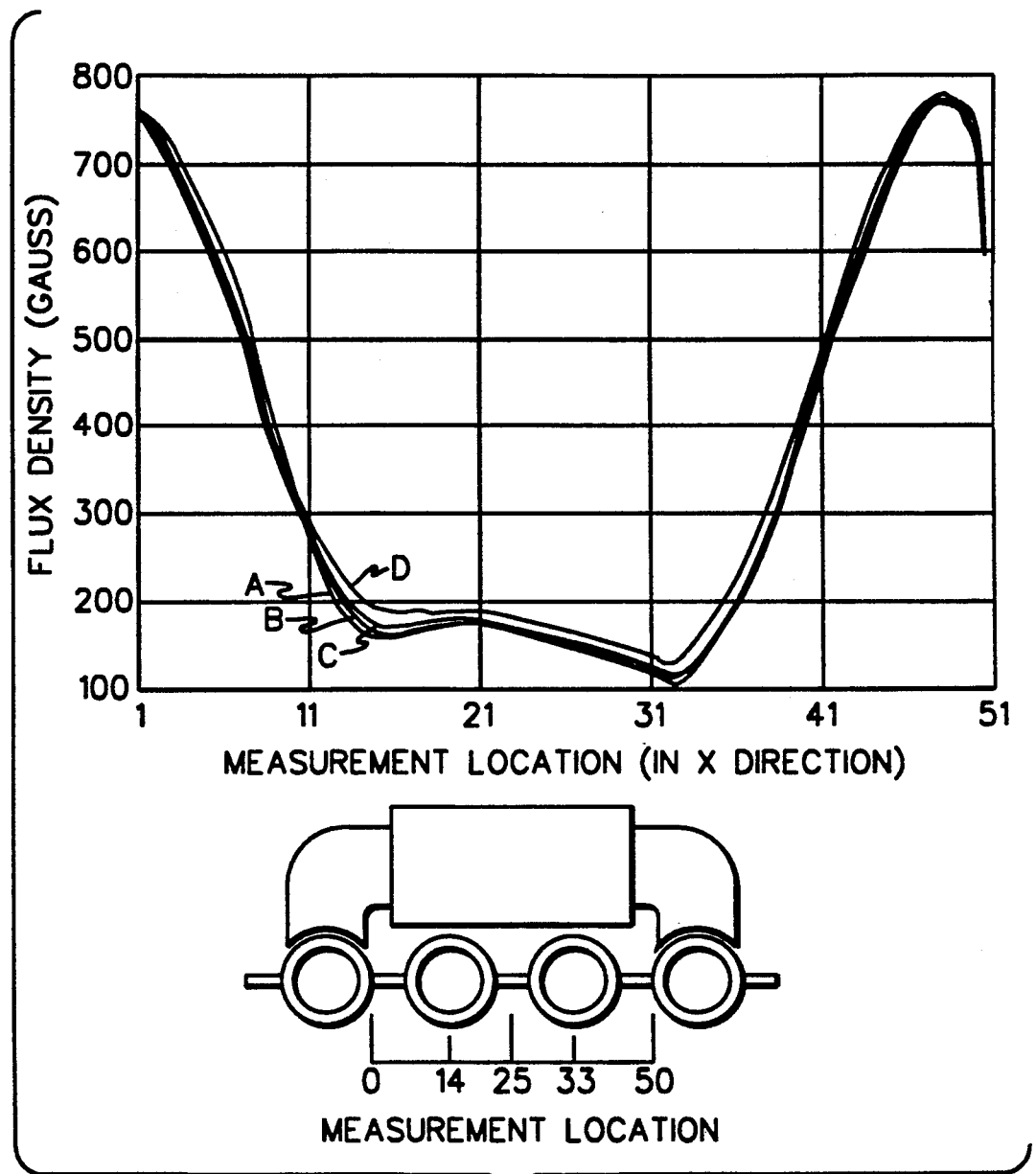
FIG. 6 is an example of the output of a device in the form of a graph of flux density in Gauss versus x displacement.

Typical graphic outputs are illustrated in FIG. 6. Lines A, B and C are plots of magnetic field contours along the x-axis in structurally sound, but dirty and distorted water wall tubes. Line D is a plot of magnetic field contour in a region having a structural flaw at the crown of the second tube.

While the invention has been particularly shown and described with reference to preferred embodiments thereof, it will be understood by those skilled in the art that other changes in form and details may be made therein without departing from the spirit and scope of the invention.

I claim:

1. An electromagnetic device for nondestructively detecting localized discontinuities in ferromagnetic objects comprising:

an adjustable direct current excitor means for generating a high intensity magnetic field;

an injector means in close proximity to said adjustable direct current excitor means for magnetically saturating a segment of a wall of a ferromagnetic object with a magnetic flux induced by said magnetic field, said injector means having two magnetic poles spaced from one another for inducing a magnetic flux above the saturation level in a segment of the object between the poles, the injector means also defining a flux return path between the poles externally of the object for completing the flux circuit;

a detector means in close proximity to said ferromagnetic object and at least partially within said magnetic flux for measuring the magnetic flux on the exterior of said ferromagnetic object and sending an output signal indicating the magnitude of said flux at a point to a signal processing means;

a plurality of position sensors mounted in close proximity to said injector means, said position sensors sending an output signal to a signal processing means indicating the relative location of said magnetic poles of said injector means with respect to said object;

a signal processing means for receiving and storing said output signals from said detector means and from said position sensors, said signal processing means being capable of calculating changes in the displacement of said injector means and being capable of generating an output signal to adjust said excitor means to compensate the amount of field being generated in order to provide a substantially constant flux in the object, being capable of comparing stored detector signals with incoming detector signals, and further capable of displaying an output; and a control mans for adjusting said excitor means according to output signals generated by said signal processing means.

2. A device according to claim 1 wherein said detector means is a Hall-effect device.

3. A device according to claim 1 wherein said detector means measures the tangential component of magnetic flux.

4. A device according to claim 1 further characterized in having two position sensors, each of said position sensors comprising an L-shaped, polarized force transducer having two ends one of which is attached to a permanent magnet and the other of which is rigidly fixed to a pole of said injector means, wherein said permanent magnet contacts said ferromagnetic object, and wherein said magnet and said sensors cooperate to indicate the position of said pole with respect to said object.

5. An apparatus for examining a water wall in a boiler comprising a device according to claim 4 and a framework, said framework providing controlled displacement of said device in three dimensions.

6. A method for testing a segment of a ferromagnetic object comprising: saturating said segment with a constant but adjustable magnetic flux, said flux being provided by a direct-current coil and a flux injector in close proximity thereto, said flux injector having two magnetic poles, each of said poles being in contact with said object at a different point on a surface of said object, thereby creating a complete flux path;

positioning a plurality of Hall-effect devices adjacent said surface of said ferromagnetic object within the path of said magnetic flux so as to detect the strength of an exterior magnetic field generated by said saturating magnetic flux;

determining the position of each pole of said flux injector in respect to said surface of said object;

adjusting said direct current supplied to said coil to compensate for a change in said position of each pole relative to said surface of said object so as to maintain a constant magnetic flux in said segment of said object; and reading an output from said plurality of Hall-effect devices to determine the contour of said exterior magnetic field.

7. A method according to claim 6 wherein a tangential component of said exterior magnetic field is detected.

* * * * *